United States Patent
Selmer et al.

(10) Patent No.: US 9,713,608 B2
(45) Date of Patent: *Jul. 25, 2017

(54) METHOD FOR TOPICALLY TREATING ACTINIC KERATOSIS ON THE TRUNK (EXCEPT CHEST) OR EXTREMITIES WITH INGENOL 3-(3,5-DIETHYLISOXAZOLE-4-CARBOXYLATE)

(71) Applicant: LEO Laboratories Limited, Dublin (IE)

(72) Inventors: Johan Selmer, Ballerup (DK); Kim Mark Knudsen, Ballerup (DK)

(73) Assignee: LEO Laboratories Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 14/524,875

(22) Filed: Oct. 27, 2014

(65) Prior Publication Data
US 2015/0258071 A1    Sep. 17, 2015

(30) Foreign Application Priority Data

Oct. 25, 2013  (EP) .................................... 13190223
Mar. 26, 2014  (EP) .................................... 14161730
Apr. 23, 2014  (EP) .................................... 14165659

(51) Int. Cl.
| A61K 31/422 | (2006.01) |
| A61K 9/06 | (2006.01) |
| A61K 9/00 | (2006.01) |
| A61K 31/4155 | (2006.01) |
| A61K 31/41 | (2006.01) |

(52) U.S. Cl.
CPC .......... *A61K 31/422* (2013.01); *A61K 9/0014* (2013.01); *A61K 9/06* (2013.01); *A61K 31/41* (2013.01); *A61K 31/4155* (2013.01)

(58) Field of Classification Search
USPC ........................................................ 514/378
See application file for complete search history.

(56) References Cited

U.S. PATENT DOCUMENTS

| 8,536,163 | B2 | 9/2013 | Brown et al. |
| 8,716,271 | B2 | 5/2014 | Brown et al. |
| 8,735,375 | B2 | 5/2014 | Brown et al. |
| 9,422,309 | B2 | 8/2016 | Liang et al. |
| 2014/0249218 | A1 | 9/2014 | Ogbourne |
| 2014/0303150 | A1* | 10/2014 | Grue-Sorensen ..... C07C 271/34 514/217.11 |
| 2015/0119433 | A1 | 4/2015 | Selmer et al. |
| 2015/0119434 | A1* | 4/2015 | Selmer ................. A61K 31/422 514/378 |
| 2015/0133542 | A1 | 5/2015 | Norrelund |
| 2015/0258071 | A1 | 9/2015 | Selmer et al. |
| 2015/0265567 | A1 | 9/2015 | Skov et al. |
| 2015/0291551 | A1 | 10/2015 | Grue-Sorensen et al. |
| 2015/0335606 | A1 | 11/2015 | Arvidsson et al. |
| 2016/0089362 | A1 | 3/2016 | Selmer et al. |
| 2016/0228396 | A1 | 8/2016 | Ladefoged et al. |

FOREIGN PATENT DOCUMENTS

WO    2012/083953    6/2012

OTHER PUBLICATIONS

Anderson et al. "Randomized, double-blind, double-dummy, vehicle-controlled study of ingenol mebutate gel 3.035% and 0.05% for actinic keratosis," J Am Acad Dermatol, 2009; 60:934-943.

Siller et al., "PEP005 (ingenol mebutate) gel, a novel agent for the treatment of actinic keratosis: Results of a randomized, double-blind, vehicle-controlled, multicenter, phase IIa study," Australian Journal of Dermatology, Australian College of Dermatologists, 50(1):16-22, Feb. 2009.

International Search Report and Written Opinion in International Application No. PCT/IB2014/002951, mailed Mar. 31, 2015, 7 pages.

International Search Report and Written Opinion in International Application No. PCT/IB2014/002940, mailed Mar. 27, 2015, 7 pages.

International Search Report and Written Opinion in International Application No. PCT/IB2014/002970, mailed Mar. 26, 2015, 7 pages.

U.S. Appl. No. 14/524,738, filed Oct. 27, 2014, Johan Selmer.
U.S. Appl. No. 14/524,731, filed Oct. 27, 2014, Johan Selmer.

* cited by examiner

*Primary Examiner* — Kristin Vajda

(74) *Attorney, Agent, or Firm* — Fish & Richardson P.C.

(57) ABSTRACT

The invention relates to the treatment of actinic keratosis on the trunk (except chest) or Extremities with ingenol 3-(3,5-diethylisoxazole-4-carboxylate).

27 Claims, 1 Drawing Sheet

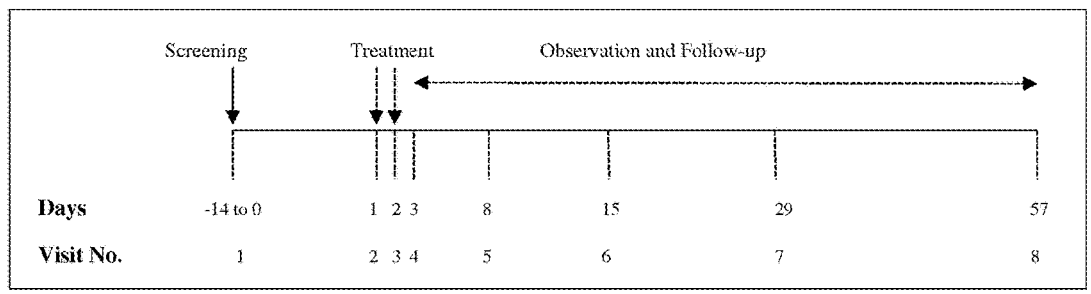

METHOD FOR TOPICALLY TREATING ACTINIC KERATOSIS ON THE TRUNK (EXCEPT CHEST) OR EXTREMITIES WITH INGENOL 3-(3,5-DIETHYLISOXAZOLE-4-CARBOXYLATE)

FIELD OF THE INVENTION

The invention relates to the treatment of actinic keratosis on the trunk (except chest) or Extremities with ingenol 3-(3,5-diethylisoxazole-4-carboxylate).

CROSS-REFERENCE RELATED APPLICATIONS

This application for U.S. patent claims priority to EP patent application No. 13190223.1, filed 25 Oct. 2013, the contents of which is incorporated herein by reference in its entirety, EP patent application No. 14161730.8, filed 26 Mar. 2014, the contents of which is incorporated herein by reference in its entirety, and EP patent application No. 14165659.5, filed 23 Apr. 2014, the contents of which is incorporated herein by reference in its entirety.

BACKGROUND

The active compound, ingenol 3-(3,5-diethylisoxazole-4-carboxylate), of the present invention is previously been described in PCT/DK2011/000154. The ingenol 3-(3,5-diethylisoxazole-4-carboxylate) is studied with respect to safety and tolerability for field therapy in 25 cm² on 4 separate areas on the forearm in concentrations of 0.025%, 0.05% and 0.075% in a gel formulation.

Existing topical treatments for actinic keratosis comprises different dosage regimens. All of them extend over weeks and months. Picato® which is launched in many countries around the world for treatment of actinic keratosis has a dosage regimen of two or three days depending on the location of the actinic keratosis and also the concentration of the active compound differs depending on the location of the actinic keratosis. According to the FDA label for Picato®, the size of the treatment area is limited to about 25 cm2 (2 inches×2 inches).

SUMMARY OF THE INVENTION

The present invention provides a topical treatment regimen with ingenol 3-(3,5-diethylisoxazole-4-carboxylate) for actinic keratosis (AK), which is of short duration and applicable to a large skin area on trunk (except chest) or extremities. Thus, the present invention provides for a compound different from the active compound, ingenol mebutate, in Picato® in a dosage regimen which is optimized for trunk or extremities.

The treatment is simple by the two day regimen. The treatment is directed against treating nonhyperkeratotic actinic keratosis. The treatment is optimized towards acceptable side-effects in terms of measured local skin reactions (LSR).

The present invention also provides a method of treating a subject diagnosed with actinic keratosis on the balding scalp, said method comprising applying an effective amount of active compound to a treatment area for two days to achieve reduction in the number of the actinic keratosis in the treated area.

BRIEF DESCRIPTION OF THE FIGURE

FIG. 1 is a schematic overview of a phase I exploratory trial design.

DETAILED DESCRIPTION OF THE INVENTION

From Picato® and other topical agents used in the treatment of actinic keratosis, it is well known that differences in treatment efficacy exists between different anatomical regions. Regions like scalp, trunk (except chest) and extremities are more difficult to treat than face. From Picato® studies have shown that local skin reactions after a given dose are milder on difficult to treat anatomical regions than on anatomical regions more easily treated with the compound. For these reasons the present invention optimizes the treatment of the trunk (except chest) and extremities only. The present invention simplifies prior and existing treatments by a simple two day regimen independent of the location of the actinic keratosis.

The present invention describes treatment of actinic keratosis on the trunk (except chest) and extremities with ingenol 3-(3,5-diethylisoxazole-4-carboxylate).

The lesions are not of atypical clinical appearance such as for example hypertrophic, hyperkeratotic or cutaneous horns and/or recalcitrant diseases, such as non-responding to cryotherapy on two previous occasions.

Local skin reactions (LSRs) occurs sometimes in the treated area. Often LSRs are quantified by a scale evaluating the following types of skin reactions: erythema, flaking/scaling, crusting, swelling, vasiculation/pustulation, and erosion/ulceration which are categorized into categories 0-4 depending on the severity of the reactions.

In the trial pre-defined grades of LSRs will constitute Dose Limiting Toxicity. The level of skin reactivity constituting dose limiting toxicity (DLT) does not reflect safety concerns but represent what dermatologists consider limits for peak levels of acceptable visible skin reactions.

Dose Limiting toxicity (DLT) is defined as:
crusting Grade 4
Erosion/ulceration Grade 4
visiculation/pustulation Grade 4 or
Two or more of the following five LSRs:
Crusting Grade 3
Swelling grade 4
Erosion/ulceration Grade 3
vesiculation/pustulation Grade 3 or
other clinically relevant signs or symptoms observed, which the
Investigator judges to be counted as a DLT.

Maximum tolerated dose (MTD) is declared as the highest dose level at which less than 4 subjects out of experience a DLT.

The study is designed in two parts:
Part 1 is a dose escalation study conducted with a once daily application of trial medication for two consecutive days and continue until the MTD is identified.

Dose escalation will only proceed if the safety and tolerability data of the subject up to day 8 is reviewed and considered satisfactory. The treatment consists of once daily treatment for 2 consecutive days. The starting dose is about 0.025% and the doses are administered in an escalating manner following review of safety and tolerability. Up to 5 different doses may be investigated in cohorts of 1 subject. The number of subjects in each cohort will depend on the number of observed DLTs. However, the MTD will always be confirmed in a cohort of 12 subjects.

Part 2 is a study of the efficacy of the MTD level identified in part 1 and the level below the identified level. Lower levels can however be chosen instead for Part 2. The outcome for Part 2 is efficacy in clearance of the AK.

The trial medication applied is preferably a gel. The gel formulation comprises: isopropyl alcohol, hydroxyethyl cellulose, benzyl alcohol, citric acid monohydrate, sodium citrate dehydrate and water and active compound in various concentrations.

The active compound is ingenol 3-(3,5-diethylisoxazole-4-carboxylate).

The present invention also relates to the treatment of actinic keratosis lesions on full balding scalp by a once daily, two day treatment.

The invention relates to the treatment of actinic keratosis lesions in an area of up to approximately 250 $cm^2$ on the trunk (except chest) or extremities in a two day treatment.

In an embodiment according to the present invention, the two day treatment is two consecutive days.

In another embodiment of the present invention, the present invention provides a method of treating a subject diagnosed with actinic keratosis, said method comprising applying an effective amount of the ingenol 3-(3,5-diethylisoxazole-4-carboxylate) to a treatment area for two days to achieve reduction in the number of actinic keratosis lesions in the treatment area.

In another embodiment of the present invention, the present invention provides a method of treating a subject diagnosed with actinic keratosis, said method comprising applying an effective amount of the ingenol 3-(3,5-diethylisoxazole-4-carboxylate) to a treatment area for two days to achieve reduction in the number of actinic keratosis lesions in the treatment area.

In yet a further embodiment of the present invention, the present invention provides the method according to the above, wherein the effective amount of the ingenol 3-(3,5-diethylisoxazole-4-carboxylate) is applied in a gel formulation from a dosage strength formulation of ingenol 3-(3,5-diethylisoxazole-4-carboxylate) of between about 0.01% and about 0.1%.

EXAMPLE 1

Subjects who qualify for Part 1 of the trial must have 5 to 20 actinic keratosis on the arm between wrist and shoulder. To be included in the trial part 2 the subjects must have 520 clinically typical, visible and discrete actinic keratosis on the trunk (except the chest) or extremities.

Part 1: Trial medication, ingenol 3-(3,5-diethylisoxazole-4-carboxylate) gel, will be applied to the treatment area once daily for two consecutive days until the maximum tolerated dose has been reached for each formulation. Up to five different doses of active compound in gel may be investigated in cohorts 12 subjects. Predefined grades of Local Skin Responses (LSRs) will constitute dose limiting toxicity (DLT). The maximum tolerated dose is defined as the highest dose level at which less than 4 out of 12 subjects experience a Dose limiting toxicity.

The doses will be administered in an escalating manner following review of safety and tolerability data performed by the dose escalation committee. Evaluation of the safety and tolerability data will be performed after Visit 5/day 8. Then subjects will be followed for 8 weeks after first application of investigational product.

Part 2 of the trial includes a total of 124 subjects: 62 subjects in each of the 2 active treatment arms (Part 1 identified Maximum tolerated dose and the dose below) and additionally 31 subjects in a vehicle arm.

To be included in the trial, Part 1, the subjects must be at least 18 years of age. Exclusion criteria is incompletely healed wound, basal cell carcinoma or squamous cell carcinoma within 5 cm of treatment area, or prior treatment with ingenol mebutate gel on the treatment area, or atypical clinical appearance on the lesions such as hypertrophic, hyperkeratotic or cutaneous hors, and/or recalcitrant disease such as non-responding to cryotherapy on two previous occasions. Also other skin conditions, cosmetic procedures or other disease or medication which could interfere with the evaluation of the trial medication or the assessments of the treated area are exclusion criteria, as is other disease or medical conditions which make the subject unsuitable to participate in the trial.

The patients are scheduled for 6 visits:
Visit 1: within 35 days prior to day 1
Visit 2: day 1 (application of trial medication)
Visit 3: day 2 (application of trial medication)
Visit 4: day 3
Visit 5: day 8 (±1 day)
Visit 6: week 2
LSRs are evaluated at all visits following visit 1.

An Evaluable Subjects analysis set will be defined as all subjects who receive at least one dose, and have LSRs recorded at all visits up to and including day 8 or have experienced a DLT at one or more visits up to and including day 8. Safety analyses will be based on the safety analysis set, which is defined as all subjects who receive at least one application of trial medication and have safety information available post treatment.

In Part 2 the patients are scheduled for 7
visits: Visit 1: within 21 days prior to day 1
Visit 2: day 1 (application of trial medication)
Visit 3: day 2 (application of trial medication)
Visit 4: day 3
Visit 5: day 8 (±1 day)
Visit 6: week 2 Visit 7: week 8
LSRs are evaluated at all visits following visit 1. AK lesion counts are performed on visit 6 and 7.

Efficacy analyses will be based on the full analysis set, which will be defined as all randomised subjects. Per protocol analysis set will be used as an efficacy subset and will be defined as subjects in the full analysis set who complete the study without major protocol deviations. Safety analyses will be based on the safety analysis set, which is defined as all subjects who receive at least one application of trial medication and have safety information available post treatment.

At visit 7 in week 8 the ratio of number of lesions at week 8 relative to baseline will be tabulated by treatment group and analyzed using a negative binomial regression on actinic keratosis count at week 8 with the log baseline value as an offset variable and treatment group and analysis site as factor. The rate ratios and the corresponding 95% confident intervals will be estimated from this model comparing the active groups pairwise. Complete clearance of AKs at week 8 will be analysed by log binomial regression with factors: Treatment group and analysis site. The number of baseline lesions will be included as a continuous variable. The rate ratios of pairwise treatment groups will be presented together with their 95% confidence intervals. Partial clearance, defined as 75% or greater reduction in AK count will be analysed in the same way as complete clearance.

The incidence and grade of LSRs will be summarized by treatment arm overall at each visit. Local skin response grades will be summarized by frequency counts and descriptive statistics by treatment arm for each of the six individual LSRs: erythema, flaking/scaling, crusting, swelling, vesiculation/pustulation, and erosion/ulceration.

A composite score will be obtained by summing the six individual LSR scores at each visit. The composite score and change from baseline will be summarized by treatment arm at each visit using descriptive statistics.

EXAMPLE 2

Safety and Tolerability of Three Concentrations of ingenol 3-(3,5-diethylisoxazole-4-carboxylate) for Field Therapy in the Treatment of Actinic Keratosis on the Forearm Compared to Ingenol Mebutate Gel 0.05%

A Phase 1 exploratory trial evaluating safety and tolerability of topical administration of ingenol 3-(3,5-diethylisoxazole-4-carboxylate) gel, 0.025%, 0.05% and 0.075% compared to ingenol mebutate gel 0.05% applied on two consecutive days to four separate 25 $cm^2$ treatment areas on the forearms of subjects with actinic keratosis (field therapy). A single-centre, randomised, active controlled, intra-patient controlled, investigator blind trial.

Actinic Keratosis (AK) is a common skin condition visible as thickened, cornified, more or less scaly lesions, often asymptomatic and characterised histopathologically by proliferation of atypical keratinocytes. It is estimated that AK occurs in 11-50% of the population aged 40 and older in the US and Australia, while the prevalence rate in Europe is 11-25%. Patients with AK tend to have Fitzpatrick skin type I or II (fair skin) which burns with sun exposure and does not tan or tans minimally.

In the context of AK, adjacent AKs may merge into one another producing a field of abnormal skin. Such 'field cancerisation' is characterised by the epithelial surface of the photo-damaged area being susceptible to the development of additional AKs or a malignancy. This is evidenced by the presence of multiple subclinical and clinically visible AK lesions as well as multifocal preneoplastic changes with genetic mutations. There is also increasing evidence that AK represents squamous cell carcinoma (SCC) in situ in its earliest stages. Histopathological evidence shows that contiguous AK is present in 97% of SCC lesions on sun-damaged skin. AK is linked epidemiologically to development of SCC (14), and both conditions share specific gene expression. If left untreated, AK may progress to SCC, with significant morbidity and death.

Ingenol 3-(3,5-diethylisoxazole-4-carboxylate) is an ingenol analogue, manufactured by a semi-synthetic process from ingenol, and developed and formulated for the field treatment of AK. Ingenol 3-(3,5-diethylisoxazole-4-carboxylate) is in the initial phase of its clinical development programme, while ingenol mebutate, another ingenol analogue, has been approved in the USA, EU, Brazil, Australia, and Canada as a field treatment for AK on the face and scalp, trunk and extremities under the brand name of Picato®. The vehicle formulation of ingenol 3-(3,5-diethylisoxazole-4-carboxylate) gel is the same as the vehicle formulation of ingenol mebutate gel. This gel formulation does not contain any inactive ingredients that would result in acute toxicity to the skin and is water soluble.

The exact mechanism of action of ingenol 3-(3,5-diethylisoxazole-4-carboxylate) continues to be investigated, but it is believed that ingenol 3-(3,5-diethylisoxazole-4-carboxylate) has a dual mechanism of action inducing cell death as well as stimulation of immune response. The preclinical safety and tolerability profile of ingenol 3-(3,5-diethylisoxazole-4-carboxylate) is similar to that of ingenol mebutate, but in vivo studies in mice where effects on dermal tumours have been evaluated suggest that ingenol 3-(3,5-diethylisoxazole-4-carboxylate) is more efficacious than ingeno mebutate in eliminating dermal tumours.

This phase 1 trial is a first in human exploratory single-centre clinical trial aiming to demonstrate the safety and tolerability of three concentrations of ingenol 3-(3,5-diethylisoxazole-4-carboxylate) (0.025%, 0.05%, and 0.075%) compared to ingenol mebutate gel 0.05% when applied topically once daily for two consecutive days to four separate 25 cm2 treatment areas (5×5 cm) containing AKs on the extensor (dorsal) aspect of the forearms. It is presently believed that ingenol 3-(3,5-diethylisoxazole-4-carboxylate) has a higher efficacy and/or milder LSR profile than ingenol mebutate.

Primary Objective

To demonstrate the safety and tolerability of three ingenol 3-(3,5-diethylisoxazole-4-carboxylate) gel concentrations (0.025%, 0.05%, and 0.075%) as compared to ingenol mebutate gel 0.05% when applied topically once daily for two consecutive days to four separate 25 $cm^2$ treatment areas (e.g. 5×5 cm) containing AKs on the extensor (dorsal) aspect forearms across the 8-week trial period.

Secondary Objective

To evaluate treatment responses on AKs of the three concentrations of ingenol 3-(3,5-diethylisoxazole-4-carboxylate) gel compared to the ingenol mebutate gel as assessed by reduction in number of clinically visible selected AK lesions eight weeks after treatment.

Trial Overview

To evaluate treatment responses on AKs of the three concentrations of ingenol 3-(3,5-diethylisoxazole-4-carboxylate) gel compared to the ingenol mebutate gel as assessed by Reflectance Confocal Microscopy (RCM) scoring of the clinically visible selected AK lesions before and eight weeks after treatment.

This was a phase 1, single-centre, randomised, active controlled, intra-patient controlled, investigator blinded trial with intra-individual comparisons to explore the safety and tolerability of ingenol 3-(3,5-diethylisoxazole-4-carboxylate) gel 0.025%, 0.05%, and 0.075% compared to ingenol mebutate gel 0.05% applied once daily for two consecutive days on the forearms of subjects with AK.

The trial population included 40 subjects at least 18 years of age with 12-16 clinically typical, visible, discrete, non-keratotic AK lesions (referred to as selected AK lesions) suitable for RCM within four separate 25 $cm^2$ (5×5 cm) selected treatment areas (STAs) on the dorsal aspects of the forearms. Each STA was to be separated by at least 5 cm from other STAs.

Whenever possible, four visible and discrete selected AK lesions are identified within each of the four STAs. However, one STA with three selected AK lesions is acceptable for a subject. The selected AK lesions are assessed by RCM. If a selected AK lesion could not be confirmed as an AK lesion by RCM, another STA with selected AK lesions has to be identified. In addition, each subject is to have one subclinical AK lesion suitable for RCM within each STA (these subclinical AKs are referred to as selected subclinical AK lesions).

STAs containing no or few keratotic lesions are preferred.

For each eligible subject, the four STAs are randomised to receive one of four of the investigational product (IP or IPs):

ingenol 3-(3,5-diethylisoxazole-4-carboxylate) gel 0.025% ingenol 3-(3,5-diethylisoxazole-4-carboxylate) gel 0.05% ingenol 3-(3,5-diethylisoxazole-4-carboxylate) gel 0.075%

Ingenol mebutate gel 0.05%

Each IP is to be applied to one of the four STAs on each subject according to random assignment on two consecutive days (Day 1 and Day 2). This ensured that all subjects are treated with the four products on both treatment days. A schematic overview of the trial design is summarised in FIG. 1. The trial consisted of three periods, a screening period, a treatment period, and an observation and follow-up period.

The trial consisted of three periods, a screening period, a treatment period, and an observation and follow-up period which are briefly described below. All subjects signed the trial-specific consent form in the presence of the investigator or his/her designee prior to any trial procedures taking place. This process is performed during the screening period.

The trial is designed as a phase 1, single-centre, randomised, active controlled, intra-patient controlled, investigator blinded trial with intra-individual comparisons to explore the safety and tolerability of ingenol 3-(3,5-diethylisoxazole-4-carboxylate) gel 0.025%, 0.05%, and 0.075% as compared to ingenol mebutate gel 0.05% applied once daily for two consecutive days on the forearms of subjects with AK. Although the number of included subjects is rather low, the intra-individual comparison design will eliminate the variability between subjects.

Ingenol mebutate gel has recently been approved as Picato® for field therapy treatment of AK in the USA, EU, Brazil, Australia, and Canada. Picato® contains the active ingredient ingenol mebutate which is an ingenol analogue. The duration of treatment with ingenol mebutate gel is two to three consecutive days which provides an advantage for treatment compliance and patient convenience. The duration of treatment required for currently marketed topical products ranges from 2 to 16 weeks. It has been previously documented that longer treatment durations reduce patient compliance.

Treatments Administered

All subjects are to be treated with all four of the IPs:
ingenol 3-(3,5-diethylisoxazole-4-carboxylate) gel 0.025% ingenol 3-(3,5-diethylisoxazole-4-carboxylate) gel 0.05% ingenol 3-(3,5-diethylisoxazole-4-carboxylate) gel 0.075%

Ingenol mebutate gel 0.05%

Each IP is applied to one of the four STAs on each subject according to random assignment on two consecutive days (Day 1 and Day 2). The IPs are applied by a specified investigational staff member in the clinical study protocol. Subjects are instructed about post-treatment care and provided with a patient safety and study medication instruction sheet.

Investigational Products

Details of the IPs are given in Table 1 and Table 2 below.
Table 1 Identity of Ingenol 3-(3,5-diethylisoxazole-4-carboxylate) Gel:
 Formulation: Hydro alcoholic gel
 Active ingredient name/strength: ingenol 3-(3,5-diethylisoxazole-4-carboxylate) 0.025%, 0.05% and 0.075% all w/w
 Excipients: Isopropyl alcohol Ph. Eur., Hydroxyethyl cellulose Ph. Eur., Benzyl alcohol Ph. Eur., Citric acid monohydrate Ph. Eur., Sodium citrate dihydrate Ph. Eur., Purified water USP.

Table 2 Identity of Ingenol Mebutate Gel:
 Formulation: Hydro alcoholic gel
 Active ingredient name/strength: Ingenol mebutate 0.05%
 Excipients: Isopropyl alcohol Ph. Eur., Hydroxyethyl cellulose Ph. Eur., Benzyl alcohol Ph. Eur., Citric acid monohydrate Ph. Eur., Sodium citrate dihydrate Ph. Eur., Purified water USP.

The IPs are stored in a refrigerator at about 2° C.-about 8° C. (36° F.-46° F.) in a secure and restricted access area.
Timing of Dose Minimum of about 16 hours are to pass between the first and the second application of IP.
Trial Discussion This trial is a first in human exploratory clinical trial aiming to compare the safety and tolerability of three concentrations of ingenol 3-(3,5-diethylisoxazole-4-carboxylate) gel (0.025%, 0.05%, and 0.075%) with ingenol mebutate gel 0.05% when applied topically once daily for two consecutive days to four separate 25 cm2 treatment areas containing AKs on the forearms.

The trial is conducted as planned in the clinical study protocol. A total of 40 subjects are randomised in this trial and demographics and baseline characteristics of the trial population are in line with the intentions of the protocol. Due to the specified inclusion criteria the trial population consisted primarily of elderly men with fair skin and large number of AKs. Almost all (95%) had a history of skin cancer and all had previously been treated for AK. Except for one subject for which treatment is reallocated, all subjects included in the trial received all planned doses of ingenol 3-(3,5-diethylisoxazole-4-carboxylate) and ingenol mebutate and all subjects completed the trial.

The primary objective of the trial is to compare the safety and tolerability of ingenol 3-(3,5-diethylisoxazole-4-carboxylate) to ingenol mebutate gel and overall the safety and tolerability profile of ingenol 3-(3,5-diethylisoxazole-4-carboxylate) is similar to ingenol mebutate gel.

No safety signals are identified from ECG, vital signs and laboratory assessments (biochemistry, haematology).

The LSR profile of ingenol 3-(3,5-diethylisoxazole-4-carboxylate) is similar to ingenol mebutate gel; mean composite LSR scores are peaked at Week 1 and are below baseline at Week 8. This pattern is in line with what is seen in previous trials with ingenol mebutate.

The AE profile of ingenol 3-(3,5-diethylisoxazole-4-carboxylate) is also similar to ingenol mebutate gel. There is no difference in the incidence of AEs inside STAs and the most common treatment related Aes are pruritus, burning sensation and tenderness. Four SAEs of SCC are reported by three subjects. Two of these events are within a ingenol 3-(3,5-diethylisoxazole-4-carboxylate) treated area and two within ingenol mebutate treated areas, despite the fact that the number of fields treated with ingenol 3-(3,5-diethylisoxazole-4-carboxylate) is approximately three times higher than the number of ingenol mebutate gel treated fields. There is also one event of Bowen's disease inside an ingenol 3-(3,5-diethylisoxazole-4-carboxylate) treated area. This is reported as a possibly related AE by the investigator and reclassified to a SAE by the sponsor.

The number of neoplastic skin tumours occurring at Week 8 inside treatment areas is unexpected but it should be noted that the subjects included in the trial are mostly elderly men, 95% of the subjects had a history of skin cancer, and 26 clinically suspected neoplastic tumours are identified also outside the STAs over a period of eight weeks. For these reasons the trial population can be considered as a very high-risk population for non-melanoma skin cancer.

Treatment efficacy is included as a secondary endpoint and assessed by change in number of clinically visible AK lesions from baseline to 8 weeks after treatment and change in RCM scores from baseline to 8 weeks after treatment. Overall, the efficacy of ingenol 3-(3,5-diethylisoxazole-4-carboxylate) is similar to ingenol mebutate gel.

Complete clinical clearance increased with increasing concentrations of ingenol 3-(3,5-diethylisoxazole-4-carboxylate).

In general, it is believed that there is no difference between ingenol 3-(3,5-diethylisoxazole-4-carboxylate) and ingenol mebutate gel in the change of RCM scores. Overall, the honeycomb pattern of lesions improved, keratosis decreased, and the thickness of stratum corneum and viable epidermis decreased. Similar results were seen for clinically visible AK lesions and subclinical lesions.

OVERALL CONCLUSIONS

In conclusion, in this exploratory clinical trial, the safety and efficacy of ingenol 3-(3,5-diethylisoxazole-4-carboxylate) gel is similar to ingenol mebutate gel 0.05% in the treatment of AK on the forearms, with a tendency of higher clearance of AK lesions seen with increasing concentration of ingenol 3-(3,5-diethylisoxazole-4-carboxylate).

INCORPORATION BY REFERENCE

The entire contents of all patents, published patent applications and other references cited herein are hereby expressly incorporated herein in their entireties by reference.

EQUIVALENTS

Those skilled in the art will recognize, or be able to ascertain using no more than routine experimentation, numerous equivalents to the specific procedures described herein. Such equivalents are considered to be within the scope of this invention and are covered by the following claims.

What is claimed is:

1. A method of treating a subject diagnosed with actinic keratosis on the trunk (except chest) or extremities, said method comprising applying a formulation comprising an effective amount of ingenol 3-(3,5-diethylisoxazole-4-carboxylate) to a treatment area having a size of between about 25 cm$^2$ and about 250 cm$^2$ on the trunk (except chest) or extremities.

2. The method of claim 1, wherein the method provides a reduction in the number of actinic keratosis lesions in the treatment area.

3. The method of claim 1, wherein ingenol 3-(3,5-diethylisoxazole-4-carboxylate) is applied once a day for two days.

4. The method of claim 1, wherein the effective amount of the ingenol 3-(3,5-diethylisoxazole-4-carboxylate) in the formulation is between about 0.01% and about 0.1%.

5. The method of claim 1, wherein the formulation comprises about 0.018%, about 0.025%, about 0.037%, about 0.05%, about 0.075% or about 0.1% of the ingenol 3-(3,5-diethylisoxazole-4-carboxylate).

6. The method of claim 1, wherein the amount of the ingenol 3-(3,5-diethylisoxazole-4-carboxylate) applied is between about 0.162 mg ingenol 3-(3,5-diethylisoxazole-4-carboxylate)/per day/about 250 cm$^2$ treatment area and about 0.9 mg ingenol 3-(3,5-diethylisoxazole-4-carboxylate)/per day/about 250 cm$^2$ treatment area.

7. The method of claim 1, wherein the ingenol 3-(3,5-diethylisoxazole-4-carboxylate) is formulated in a gel.

8. The method of claim 1, wherein the ingenol 3-(3,5-diethylisoxazole-4-carboxylate) is topically applied in a concentration of from about 0.018% to about 0.1% of the formulation.

9. The method of claim 7, wherein the ingenol 3-(3,5-diethylisoxazole-4-carboxylate) is topically applied in a concentration of from about 0.018% to about 0.1% of the formulation.

10. A method of treating a subject diagnosed with actinic keratosis on the trunk (except chest) or extremities, said method comprising topically applying a formulation comprising an effective amount of ingenol 3-(3,5-diethylisoxazole-4-carboxylate) to a treatment area on the trunk (except chest) or extremities,
   wherein said method provides a reduction in the number of actinic keratosis lesions in the treated area on the trunk (except chest) or extremities, wherein the treatment area is of a size between about 25 cm$^2$ and about 250 cm$^2$, and wherein the dosage strength of the ingenol 3-(3,5-diethylisoxazole-4-carboxylate) is between about 0.018% and about 0.1%.

11. The method of claim 2, wherein the effective amount of the ingenol 3-(3,5-diethylisoxazole-4-carboxylate) in the formulation is between about 0.01% and about 0.1%.

12. The method of claim 3, wherein the effective amount of the ingenol 3-(3,5-diethylisoxazole-4-carboxylate) in the formulation is between about 0.01% and about 0.1%.

13. The method of claim 2, wherein the formulation comprises about 0.018%, about 0.025%, about 0.037%, about 0.05%, about 0.075% or about 0.1% of the ingenol 3-(3,5-diethylisoxazole-4-carboxylate).

14. The method of claim 3, wherein the formulation comprises about 0.018%, about 0.025%, about 0.037%, about 0.05%, about 0.075% or about 0.1% of the ingenol 3-(3,5-diethylisoxazole-4-carboxylate).

15. The method of claim 2, wherein the ingenol 3-(3,5-diethylisoxazole-4-carboxylate) is formulated in a gel.

16. The method of claim 3, wherein the ingenol 3-(3,5-diethylisoxazole-4-carboxylate) is formulated in a gel.

17. The method of claim 4, wherein the ingenol 3-(3,5-diethylisoxazole-4-carboxylate) is formulated in a gel.

18. The method of claim 5, wherein the ingenol 3-(3,5-diethylisoxazole-4-carboxylate) is formulated in a gel.

19. The method of claim 6, wherein the ingenol 3-(3,5-diethylisoxazole-4-carboxylate) is formulated in a gel.

20. The method of claim 11, wherein the ingenol 3-(3,5-diethylisoxazole-4-carboxylate) is formulated in a gel.

21. The method of claim 12, wherein the ingenol 3-(3,5-diethylisoxazole-4-carboxylate) is formulated in a gel.

22. The method of claim 13, wherein the ingenol 3-(3,5-diethylisoxazole-4-carboxylate) is formulated in a gel.

23. The method of claim 14, wherein the ingenol 3-(3,5-diethylisoxazole-4-carboxylate) is formulated in a gel.

24. The method of claim 2, wherein the ingenol 3-(3,5-diethylisoxazole-4-carboxylate) is topically applied in a concentration of from about 0.018% to about 0.1% of the formulation.

25. The method of claim 3, wherein the ingenol 3-(3,5-diethylisoxazole-4-carboxylate) is topically applied in a concentration of from about 0.018% to about 0.1% of the formulation.

26. The method of claim 1, wherein ingenol 3-(3,5-diethylisoxazole-4-carboxylate) is applied once a day for two consecutive days.

27. The method of claim 10, wherein ingenol 3-(3,5-diethylisoxazole-4-carboxylate) is applied once a day for two consecutive days.

\* \* \* \* \*

UNITED STATES PATENT AND TRADEMARK OFFICE
CERTIFICATE OF CORRECTION

| | |
|---|---|
| PATENT NO. | : 9,713,608 B2 |
| APPLICATION NO. | : 14/524875 |
| DATED | : July 25, 2017 |
| INVENTOR(S) | : Johan Selmer and Kim Mark Knudsen |

It is certified that error appears in the above-identified patent and that said Letters Patent is hereby corrected as shown below:

In the Claims

In Column 10, Line 7:
In Claim 9, delete "7" and insert --4--, therefor.

Signed and Sealed this
Twenty-sixth Day of September, 2017

Joseph Matal
*Performing the Functions and Duties of the*
*Under Secretary of Commerce for Intellectual Property and*
*Director of the United States Patent and Trademark Office*